US00PP30054P3

(12) United States Plant Patent
Austin

(10) Patent No.: US PP30,054 P3
(45) Date of Patent: Jan. 8, 2019

(54) ***ROSA HYBRIDA* SHRUB NAMED 'AUSKINDLING'**

(50) Latin Name: *Rosa hybrida*
Varietal Denomination: AUSkindling

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 238 days.

(21) Appl. No.: 14/999,443

(22) Filed: May 4, 2016

(65) Prior Publication Data

US 2017/0079170 P1 Mar. 16, 2017

(30) Foreign Application Priority Data

Sep. 24, 2015 (QZ) ..... PBR 2015/2229

(51) Int. Cl.
*A01H 5/02* (2018.01)

(52) U.S. Cl.
USPC ..... Plt./103

(58) Field of Classification Search
USPC ..... Plt./103
See application file for complete search history.

*Primary Examiner* — Keith O. Robinson
(74) *Attorney, Agent, or Firm* — KPPB LLP

(57) ABSTRACT

A variety of rose plant of the shrub class, named 'AUSkindling'. The 'AUSkindling' is a variety of a rose with a long flowering season, and pretty peachy pink buds that open to reveal pure white chalice-shaped blooms. The blooms maintain their shape during wet weather and have a moderate old rose fragrance.

1 Drawing Sheet

Classification: The present invention relates to a new *Rosa hybrida* shrub of the market class 'English Rose'.

Variety denomination: The new plant has the varietal denomination 'AUSkindling'.

CROSS-REFERENCE TO RELATED APPLICATION

The present application claims priority to European CPVO 2015/2229, filed Sep. 24, 2015.

ORIGIN OF INVENTION

This invention relates to a new and distinct variety of shrub rose plant named 'AUSkindling', which was originated from the cross-pollination of the two 'unnamed' and unpatented seedlings of *Rosa hybrida.*

BACKGROUND OF THE INVENTION

The primary objective of this breeding was to produce a rose variety with a long flowering season, and having peachy buds that open to pure white, chalice-shaped blooms with a moderate old rose fragrance.

SUMMARY OF THE INVENTION

Among the features which distinguish the new variety from others presently available and commercial rose cultivars known to the inventor is the following combination of characteristics: blooms having petals white in color that are chalice-shaped; a moderate old rose fragrance; having a long flowering season; and healthy shrubbery.

Asexual reproduction of the new variety by budding as performed at Bowling Green Lane in Albrighton, Britain shows that the foregoing and other distinguishing characteristics come true to form and are established and transmitted through succeeding asexual propagations. 'AUSkindling' may be asexually propagated by budding. The budding successfully occurred on the unpatented plant/rootstock *Rosa dumetorum* 'Laxa' for the observed plants.

COMPARISON WITH PARENTS

The maternal and paternal parents of 'AUSkindling' are two unnamed seedlings. The new rose may be distinguished from its maternal parent, by the following combination of characteristics: the maternal parent is a shrub with a yellow flower. The new rose may be distinguished from its pollen parent, by the following combination of characteristics: the paternal parent has a climbing growth habit with an apricot-pink flower.

COMPARISON WITH THE CLOSEST COMMERCIALLY AVAILABLE CULTIVAR

The closest commercially available cultivar to the new variety is 'AUSprior' (U.S. Plant Pat. No. 19,465). Although both roses are white, the new rose may be distinguished from the 'AUSprior' roses. The 'AUSprior' roses have a slightly yellow hue (RHS 155B (white group)) whereas the 'AUSkindling' roses have a slightly pink hue (RHS N155D (white group)). The blooms of 'AUSprior' are also cupped with approximately 121 petals, whereas 'AUSkindling' is a similar sized bloom but with a more open cup with around 52 petals. The 'AUSprior' has buds which are RHS 1D (green-yellow group) when the sepals first divide, whereas for 'AUSkindling,'the buds first show RHS N155B (white group). Finally, 'AUSprior' has an arching, lax growth whereas 'AUSkindling' has a strong, broad open growth.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSkindling' specimens were made at the nursery at David Austin Roses Limited in Albrighton, Wolverhampton, United Kingdom. The following description is of 1 year-old rose plant of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

- *Size*.—About 3.0 cm long and 1.7 cm in diameter when the petals start to unfurl.
- *Form*.—The bud form is pointed ovoid.
- *Color*.—When sepals first divide, the bud color is RHS 145C (yellow-green group) with RHS 37C (red group). When half blown, the upper sides of the petals are RHS N155D (white group) with RHS 155A (white group), and the lower sides of the petals RHS N155D (white group) with RHS 155A (white group).
- *Calyx*.—Shape: opens to a star shape, with the sepals finally folding back against the stems. Length: 7.0 cm. Diameter: 7.0 cm.
- *Sepals*.—Arrangement: Regularly arranged. Extensions: Medium. Color: Upper Surface: RHS 146D (yellow-green group) with RHS 183C (greyed-purple group). Lower Surface: RHS 147D (yellow-green group). Length: 2.4 cm. Width: 0.9 cm. Shape: Lanceolate. Surface texture: Upper Surface: Smooth. Lower Surface: Downy. Number: There are 3 normally appendaged sepals, and 2 unappendaged sepals with hairy edges.
- *Receptacles*.—Color: RHS 146A (yellow-green group). Shape: apple. Size: small, about 0.9 cm long×0.9 cm wide. Surface: Smooth.
- *Peduncle*.—Length: Medium, averaging about 5 cm. Surface: Prickly (some very small prickles) and glandular. Color: RHS 183C (greyed-red group). Strength: Strong.

Blooms:

- *Size*.—Large, average open diameter is about 9 cm.
- *Borne*.—Several together in clusters of around 7 with blooms having a rounded shape.
- *Stems*.—Strength: Strong, average length is about 30 cm. Diameter: 4 mm.
- *Form*.—When first open, bloom is cupped. Permanence of bloom: flattens.

Petalage: Number of petals under normal conditions: 52.

- *Flower type*.—Double.
- *Color*.—The upper sides of the petals are RHS N155D (white group). The reverse sides of the petals are RHS N155D (white group). The base of the petals has no yellow spot.
- *Variegations*.—None.
- *Discoloration*.—The general tonality at the end of the first day is RHS N155D (white group), and at the end of the third day is RHS N155D (white group).
- *Fragrance*.—Moderate. Character of fragrance: Old Rose.

Petals:

- *Texture*.—Whole of petal: Smooth. Upper Surface: Smooth.
- *Size*.—Width: 3.8 cm. Length: 5.0 cm.
- *Surface*.—Smooth.
- *Shape*.—Obovate.
- *Margin*.—Entire.
- *Apex shape*.—Rounded.
- *Base shape*.—Acute.
- *Form*.—Incurved.
- *Arrangement*.—Informal.
- *Petaloids*.—Number: Around 13. Color: RHS N155D (white group). Length: 2.0-3.8 cm. Width: 0.5-1.5 cm. Shape: Obovate. Margin: Irregular.
- *Persistence*.—Petals drop off cleanly before drying.
- *Lastingness*.—On the plant: fair, about 3 days. As a cut flower: not tested.

Reproductive parts:

- *Stamens*.—Number: 70. Length: 1 cm.
- *Anthers*.—Length: 2 mm. Color: RHS 20B (yellow-orange group). Arrangement: Regular around styles.
- *Filaments*.—Color: RHS 20B (yellow-orange group). Length: 8 mm.
- *Pollen*.—Color: RHS 20A (yellow-orange group). Amount: Moderate.
- *Pistils*.—Number: 40. Length: 6 mm.
- *Styles*.—Color: RHS 160A (greyed-yellow group). Length: 4 mm.
- *Stigmas*.—Color: RHS 160A (greyed-yellow group). Length: 1 mm.
- *Hips*.—NONE Observed.

PLANT CHARACTERISTICS

Plant form: Shrub.

Plant growth: Medium, upright.

Age to maturity: 2 years.

Mature plant: Height: 120 cm. Width: 90 cm.

Rootstock: 'Dr. Huey' (unpatented) in the U.S. and *Rosa dumetorum* 'Laxa' (unpatented) for the observed plants in the UK.

Foliage:

- *Number*.—Leaflets on normal mid-stem leaves is: 5 mostly, but some have 3 leaflets (including terminal leaflet).
- *Size*.—Medium, about 12 cm long×10 cm wide.
- *Quantity*.—Normal. Number of leaves per flowering stem is: 7-10.
- *Color*.—New foliage: Upper side: RHS 146A (yellow-green group) with RHS 183C (greyed-purple group). Lower side: RHS 183C (greyed-purple group). Old foliage: Upper side: RHS 137A (green group) with RHS 137D (green group). Lower side: RHS 137D (green group).

Leaflets:

*Size*.—About 5.5 cm long×4.0 cm wide.

*Shape*.—Elliptic.

*Base shape*.—Obtuse.

*Apex shape*.—Acuminate.

*Texture*.—Upper side: Leathery.

*Glossiness*.—Strong.

*Edge*.—Serrated.

*Serrations*.—Single.

*Petiole*.—Color: RHS 146C (yellow-green group) with RHS 183C (greyed-purple group). Length: 4 cm. Width: 1.2 mm. Surface Texture: Glandular.

*Petiole rachis*.—Color: RHS 146C (yellow-green group). Underside: Smooth.

*Stipules*.—Length: 2-3 cm, glandular. Color: RHS 146C (yellow-green group).

*Auricle*.—Shape: Lanceolate. Length: 6-10 mm. Width: 2.0 mm. Color: RHS 146C (yellow-green group).

*Vein color*.—Color: Upper: RHS 137A (green group). Lower: RHS 137D (green group).

*Venation pattern*.—Reticulate.

Wood:

*New wood*.—Color: RHS 183C (greyed-purple group). Bark: Smooth.

*Old wood*.—Color: RHS 146A (yellow-green group) with some RHS 183D (greyed-purple group). Bark: Smooth.

Branching habit:

*Number*.—7.

*Branching dimension*.—Length: 45 cm. Diameter: 7 mm.

Stems:

*Mature stem*.—Length: 60 cm. Diameter: 0.7 cm.

*Internode distance*.—4 cm. The above measurements are all variable, depending on growing conditions in a season.

*Stem pubescence present*.—No.

Prickles:

*Quantity*.—On main canes from base: Few. Number per stem length: 7 per 10 cm. On laterals from main canes: Few. Number per stem length: 7 per 10 cm.

*Form*.—Deep concave.

*Length*.—8 mm.

*Color when young*.—RHS 183C (greyed-purple group).

*Color when mature*.—RHS 183C (greyed-purple group).

Small prickles:

*Quantity*.—Main stalk: None. Laterals: None.

Disease resistance:

*Powdery mildew*.—Caused by the fungus *Sphaerotheca pannosa*: Resistant.

*Downy mildew*.—Caused by species of the fungi *Peronospora, Bremia* and *Plasmopara*: Resistant.

*Blackspot*.—Caused by the fungus: *Diplocarpon*: Resistant.

*Rust*.—Cause by the fungus *Phragmidium*, including, *P. tuberculatum* and *P. mucronatum*: Resistant.

Pest resistance: Not tested.

Winter hardiness: Not tested.

Growing conditions: Normal garden conditions.

What is claimed is:

1. A new and distinct variety of rose plant of the shrub class, substantially as herein shown and described.

* * * * *

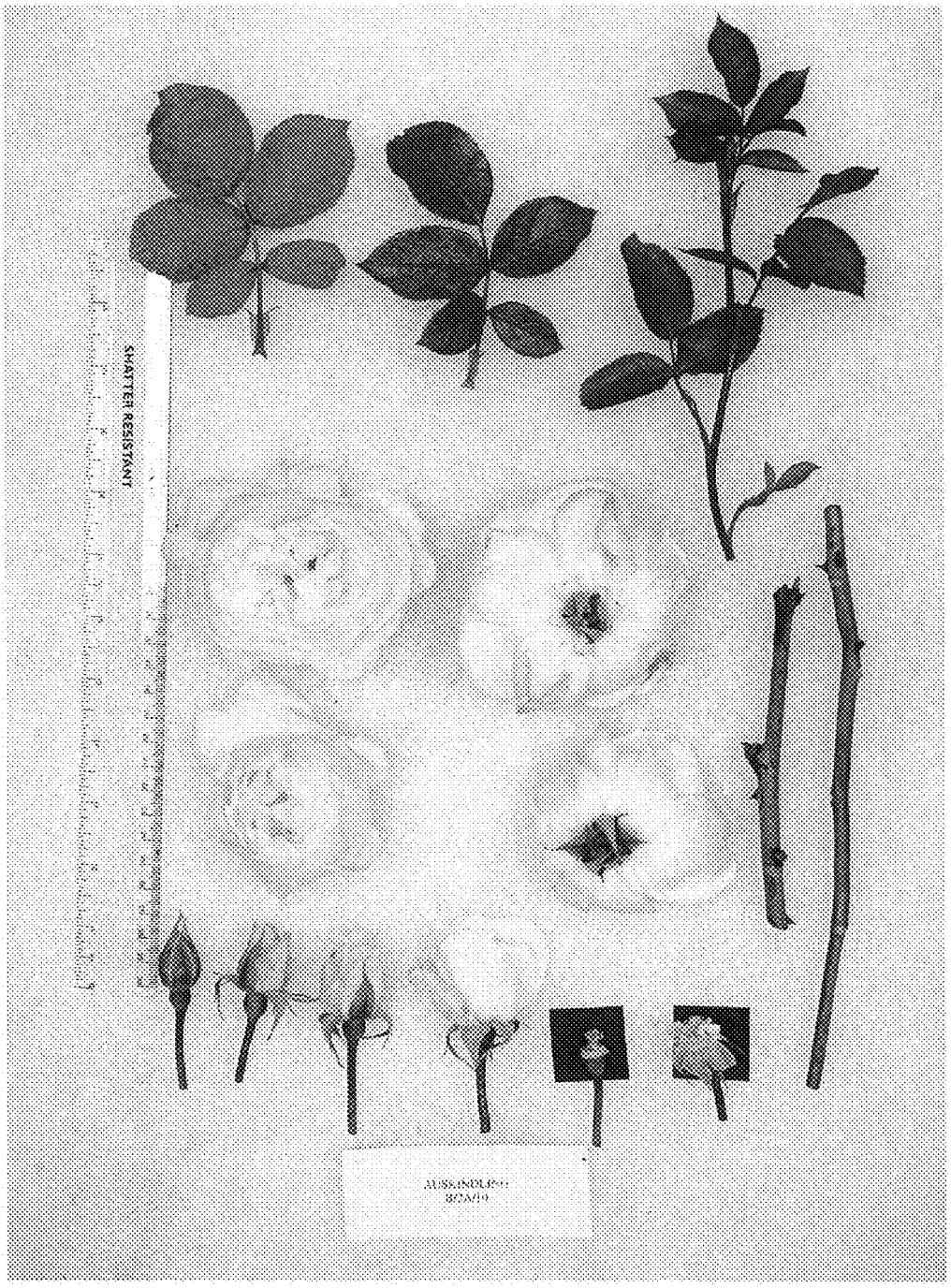
SHATTER RESISTANT
MUSKINDUP01
BGM10